United States Patent [19]

Jordan et al.

[11] Patent Number: 4,692,407
[45] Date of Patent: Sep. 8, 1987

[54] METHOD FOR THE DETERMINATION OF *STREPTOCOCCUS MUTANS*

[75] Inventors: Harold V. Jordan, Wellesley Hills, Mass.; Max Marmel, Toronto, Canada

[73] Assignee: Forsyth Dental Infirmary for Children, Boston, Mass.

[21] Appl. No.: 696,593

[22] Filed: Jan. 31, 1985

[51] Int. Cl.$^4$ .......................... C12Q 1/14; C12N 1/20
[52] U.S. Cl. ..................................... 435/36; 435/253; 435/800; 435/801; 435/299
[58] Field of Search ................. 435/36, 253, 800, 801, 435/292, 293, 294, 299, 300, 810

[56]  References Cited

U.S. PATENT DOCUMENTS

| | | | |
|---|---|---|---|
| 3,843,452 | 4/1972 | Freake et al. | 435/300 |
| 3,890,200 | 6/1975 | Jordan et al. | 435/253 |
| 4,108,728 | 8/1978 | Spinner et al. | 435/292 |
| 4,179,338 | 12/1979 | Gordon | 435/800 |
| 4,308,347 | 12/1981 | Forrer et al. | 435/300 |

FOREIGN PATENT DOCUMENTS 1061730 9/1979 Canada .
0086300 5/1982 Japan ..................................... 435/36

OTHER PUBLICATIONS

Alaluusua et al. (1984) Scand. Journal of Dental Research, vol. 92, pp. 127–133.

*Primary Examiner*—David M. Naff
*Assistant Examiner*—William J. Herald
*Attorney, Agent, or Firm*—Richard P. Crowley

[57]  ABSTRACT

A test kit and method is disclosed for the semi-quantitative detection of *Streptococcus mutans* from the oral cavity of a patient. Saliva from a patient is introduced into a diluent solution to which has been added just before the saliva a predetermined powdered amount of bacitracin. Then the diluent solution is contacted with a sterile media-coated paddle, the media-coated paddle containing the diluent and test saliva is incubated, and *Streptococcus mutans* in the test saliva is semi-quantitively determined by comparing the percent of colony density with a standard *Streptococcus mutan* colony density chart.

13 Claims, 2 Drawing Figures

BACTERIA PER ML. SALIVA.

METHOD FOR THE DETERMINATION OF *STREPTOCOCCUS MUTANS*

BACKGROUND OF THE INVENTION

A selective media has been developed for the detection and isolation of *Streptococcus mutans* from human dental plaque in the presence of other interfering microorganisms (see U.S. Pat. No. 3,890,200, issued June 17, 1975, hereby incorporated by reference in its entirety). The selective media composition for the growth of *Streptococcus mutans* comprises a solid media selective to induce the growth of the *Streptococcus mutans*, such as for example a mitis salivarius agar medium. In accordance with the invention described in the patent, the solid media must contain therein a combination of a saccharide compound, such as a mono or di saccharide compound, for example sucrose, fructose or glucose or a combination thereof, together with a selective inhibitory agent such as a polypeptide antibiotic, for example bacitracin, which inhibits the growth of interfering microorganisms, while not impeding the growth of the selective organism of determination. Thus, the saccharide and the antibiotic compounds are present together in a defined concentration insufficient to prevent the growth of *Streptococcus mutans* on the solid media, but sufficient to prevent the growth in sufficient quantities of interfering microorganisms, such as for example a concentration for the saccharide or from about 5 to 50 percent and the concentration of the antibiotic, such as bacitracin from about 0.01 to 5.0 units per milliliter.

It is desirable to provide a method and test kit for the growth and isolation of *Streptococcus mutans* and to determine the extent of growth of the *Streptococcus mutans* in order to provide an indication of the susceptibility of a patient to dental caries. Typically, the method comprises providing a selective media containing the combination of the bacitracin and the saccharide and inoculating the media with a source of *Streptococcus mutans* then growing and isolating the *Streptococcus mutans* on the media free of interfering organisms. The selective media for *Streptococcus mutans* and the method as described in the U.S. patent is both effective and suitable for use in the determination and isolation of *Streptococcus mutans* in a laboratory environment with trained laboratory personnel. However, it would be most desirable to provide for a simple and effective test kit and method for use by dentists, dental technicians and other health professionals in their office to provide for the semi-quantitative determination of *Streptococcus mutans*. A simple and effective method that is suitable for semi-quantitative determination out side of the laboratory would be useful in order to provide for a classification of patients into patients of high, intermediate and low dental caries risk. The determination of a high risk patient would enable preventative measures to be taken to reduce the patient's susceptibility to dental caries, such as the use of professional teeth cleaning, variation in diet, flouride treatment, treatment of lesions, direct antibacterial therapy such as the use of chlorhexidine or antibiotics and other preventative or therapeutic treatment.

SUMMARY OF THE INVENTION

The invention relates to a test kit and method for the semi-quantitative determination of *Streptococcus mutans*. In particular, the invention concerns a test kit and method for the semi-quantitative determination of *Streptococcus mutans* from the oral cavity of a patient, which test kit has a long shelf life and which is suitable for use by dentists and dental professionals in a non-laboratory environment.

The test kit of the invention comprises a first sealed container, such as a vial, which contains an asceptic or sterile solid selective media, and preferably a dip-slide or paddle-type flat support surface with a handle wherein at least one or both support surfaces are coated with a selective media layer comprising a solid media such as the agar, and a sufficient amount of a saccharide compound such as sucrose, in a high enough concentration insufficient to prevent the growth of *Streptococcus mutans*, but sufficient to prevent the growth of interfering microorganism. A second sealable container, such as a vial, contains an asceptic or sterile diluent solution, such as a buffered saline solution, into which solution a test sample for the determination of *Streptococcus mutans* is to be introduced, such as a saliva sample or dental plaque sample selected from the oral cavity of a patient.

The test kit also includes a separate predetermined amount and concentration of a polypeptide, particularly a dry powdered bacitracin composition, typically in tablet or capsule form, either alone or admixed with a filler, in a predetermined amount insufficient to prevent the growth of the *Streptococcus mutans*, but sufficient to prevent the growth of interfering microorganisms. The test kit also requires a composition in order to generate carbon dioxide in the presence of water to provide a carbon dioxide-containing atmosphere for the incubation of the test sample.

Typically, the test kit also includes a magnifying means to examine the surface of the solid substrate after incubation for the colony density of the *Streptococcus mutans* grown thereon, such as for example a microscope or a magnifying glass which may or may not be part of the kit, but which may be furnished or used separately. The microscopic mean is to examine the surface of the incubated solid substrate also includes techniques or means to compare the observed colony density of the *Streptococcus mutans* on the solid substrate with a comparison standard, such as for example a standard colony density chart to determine in a semi-quantitative manner, i.e. by interpolation or extrapolation, the colony density of the tested sample of the patient.

The test kit also includes an incubation container or vial adapted for the incubation of the solid substrate surfaces after contact by the diluent solution and the test sample therein, and to which diluent solution the predetermined amount of the polypeptide, such as a bacitracin composition, has been added just and usually immediately prior to use. The incubation container may be a standard incubation container or a separate container or vial, but for test kit purposes and simplicity may be and preferably is the first container or vial in which the solid substrate surface is stored, so that such first container is a container for the asceptic solid substrate, and then later becomes an incubation container.

Optionally the test kit may contain some nontoxic inert chewable substance in order to promote salivation by the patient, i.e. so as to stimulate the flow of saliva, and which substance may comprise a variety of sealed materials such as for example a plastic material, a gummy material such as a natural gum, chewing gum or a wax-type material such as a paraffin wax tablet or bar. The saliva flow composition not only stimulates saliva, but also helps to dislodge bacteria from the teeth in order to promote a more accurate test result.

The method for the semi-quantitative determination of *Streptococcus mutans* in a test sample, typically taken from the oral cavity of a patient such as a saliva, spit, etc., comprises obtaining a test sample from the patient, such as a saliva sample, after masticating on an inert chewable substance to stimulate the flow of saliva, then introducing the test sample into a predetermined volume of the asceptic saline diluent solution in the second container of the test kit, such as by the patient spitting saliva into the second container. The predetermined amount of the powdered bacitracin composition from the test kit is added to the diluent solution, preferably immediately before (or not preferred immediately after) introducing the test sample. The diluent solution with the test sample is then shaken and thereafter the solid substrate, such as a dip-slide or paddle containing a handle with the paddle or slide portion having a coated selective media on each side, containing the agar and the saccharide is then placed in the bacitracin test sample-containing diluent solution. After such contact the test slide or paddle is then removed and placed back in the first container for incubation with a carbon dioxide composition such as a solid carbon dioxide generating tablet added with a little water to provide a carbon dioxide atmosphere within the first container which is then sealed and incubated with the coated substrate therein for a defined incubation period and temperature. Thereafter the coated substrate so incubated is removed and the colony growth of the *Streptococcus mutans* is then examined, such as by a magnifying glass or a microscope or other means, and compared with a standard, such as typically a *Streptococcus mutans* density colony chart, to obtain a semi-quantitative rapid determination of the Streptococcus count per unit in the test sample.

The test kit and method thus provides an easy, effective, simple and stable technique for determining semi-quantitative detection of *Streptococcus mutans* from a test sample, such as the oral cavity, and provides for a dental professional to identify high, low or medium risk patients. The standard comparison chart may show a colony density of $10^3$, $10^4$, $10^5$, $10^6$, $10^7$ as the *Streptococcus mutans* per milliliter of the test sample, and with the colonies being shown as very dark colonies on a blue or lighter background. The dentist or dental professional on examining and comparing the test colony density with the standard comparison chart would determine that a colony density of *Streptococcus mutans* of $10^2$ would be a patient not at risk, while $10^3$ to $10^4$ would be a transition range, while any patients having a $10^5$ to $10^6$ colony density or greater would be a high risk patient and appropriate professional preventative and therapeutic steps could then be taken.

The first container of the test kit, generally a small clear plastic tube, generally ranging from say 25 to 60 millileters and generally transparent with a screw cap, and with the screw cap having a dip-slide or paddle and handle secured thereto and with the solid media coated on both sides of the paddle or slide. The media typically comprises agar such as the mitis salivarious agar, and the selective saccharide such as sucrose, together with small amounts of 0.001 to 10 weight percent of other optional additives such as peptones like meat and casein peptones to compensate for any nutritional loss in the media due to sterilization of the media, and together with pH adjustment additives, and stabilizers such as ammonium sulfate or dyes such as trypan blue, and selective agents for the bacteria such as a potassium tellurite. The media composition is made up and then subject to sterilization, then the media is dispensed onto the surface of the dip-slides or paddles and inserted into the first container. It is important that the antibiotic employed, such as the bacitracin which is a polypeptide, not be added to the media composition which is coated onto the paddle, since it has been found that the bacitracin when placed in the media, such as agar which is a water gel, then becomes hydrated and the shelf life of the bacitracin is significantly reduced to about one week or less. Therefore, in the test kit the bacitracin employed is used separately as a dry powder in a defined amount and added to the diluent prior to its use to avoid stability problems.

The second container may be similar in size to the first container, contains the diluent solution which is normally a saline solution which has been buffered to 7 or 7.5 pH, typically with the employment of water-soluble phosphate salts or hydrogen phosphates, such as potassium hydrogen phosphate, with deionized water. The dip-slide or paddle in the first container and the diluent solution in the second container are sterilized as to render the containers and the contents asceptic. While a wide variety of sterilization techniques may be employed, such as autoclaving, heat, ethylene oxide, and other techniques, it has been discovered that the irradiation of the first and second containers by a gamma ray source such as a Cobalt-60 source and generally ranging from say 1 to 3 Mrads is very effective in destroying any possible contaminants and renders the media and the diluent solution sterile together with the slide or paddle. The irradiation technique is particularly useful in that the irradiation may be employed after the media is carefully dispensed onto the paddle or dip-slides so that the irradiation can take place after the containers are packed into shipping cases.

The process of preparing the media and the diluent through the use of irradiation of the first and second containers is the preferred method for preparing the asceptic media coated slide paddles and the diluent solution. The sterilization of the first container with the paddles coated with the media by gamma ray irradiation for other purposes has been described in Canadian Pat. No. 1,061,730. However, in the process for preparing sterile culture media through irradiation, the culture media must be supplemented by specific quantities of one or more of the ingredients thereof in order to compensate for the loss of such ingredients and nutritional value due to such irradiation. Thus, where in the production of the culture media for employment onto the paddle surfaces where irradiation is employed, additional amounts of the media ingredients and a base added so the pH is adjusted to a higher alkalinity to offset the effect due to such irradiation.

The bacitracin composition employed in the test kit is added to the diluent solution just prior to the time of use, thus avoiding problems of shelf stability by providing a dry bacitracin composition typically composed of an effective amount in a predetermined quantity of bacitracin usually admixed with a dry, inert, pharmaceutically-inactive filler-type compound, such as a sorbitol. The powdered bacitracin composition may be prepared in tablet, capsule or other powder-type form to give the desired concentration of about 300 to 550, i.e. 400 to 480, bacitracin units per tablet or capsule for use per 24 milliliters of the buffered saline solution in the test kit. The bacitracin composition when added to the diluent and combined with the sucrose of the coated media is present in a concentration insufficient to prevent the growth of the *Streptococcus mutans*, but sufficient to prevent the growth of interfering microorganisms in sufficient quantity to interfere with the semi-quantitative method of determination.

The test kit also includes a composition in order to provide for the generation of carbon dioxide so that the incubation may be carried out in the carbon dioxide containing atmosphere, typically the desired amount of carbon dioxide depends on the volume of the first container employed or the incubation container as a separate container employed. Typically a powdered capsule or tablet which contains a weak acid in combination with a bicarbonate is employed, such as for example a combination of a tartaric acid with sodium bicarbonate of desired quantities to produce the desired amount of carbon dioxide. The carbon dioxide generating composition should, when placed in contact with a small amount of water, generate the carbon dioxide.

The color density comparison charts or other means, such as photographs, etc., of comparing the incubated test sample of the *Streptococcus mutans* should be visually perceptive enough so as to provide for the user to identify in a rough manner the amount of the *Streptococcus mutans* for the purposes of the test kit, that is to identify low, transition and high risk type patients.

The invention will be described for the purposes of illustration only in connection with certain specific embodiments of the test kit and method; however, it is recognized that those persons skilled in the art may make various changes, modifications, additions and improvements all falling within the spirit and scope of the invention.

DESCRIPTION OF THE EMBODIMENTS

Figure 1:
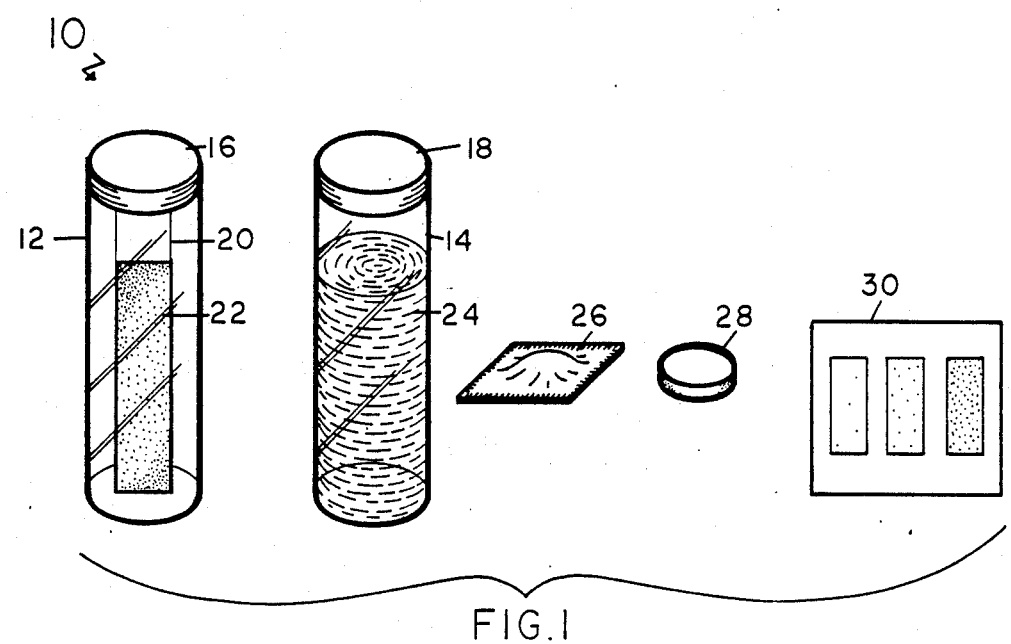
FIG. 1 is a schematic, perspective view of the components of the test kit of the invention.

FIG. 1 shows the test kit 10 which contains a first plastic, transparent vial 12 having a screw cap 16, in which vial there is a rectangular dip-slide or paddle 20 secured to the screw cap 16 and which paddle contains on both surfaces a coated media 22 containing agar and sucrose. The container 12 with the paddle 20 has been subjected to Cobalt-60 irradiation to provide for a sterile interior. The second container 14 is a transparent, plastic container which also has a screw cap 18 and which contains therein a diluent solution 24 which is a phosphate buffered saline solution, which container and solution has also been irradiated with Cobalt-60 to provide an asceptic diluent solution. A carbon dioxide gas generating compound 26 is shown enclosed in a tinfoil package which contains a mixture of tartaric acid and sodium bicarbonate. A bacitracin tablet 28 contains a mixture of bacitracin and an inert filler such as sorbitol. The test kit also includes a standard colony density comparison chart 30 through which the colony density of the incubated test sample may be compared to derive at a semi-quantitative determination of the *Streptococcus mutans*.

Figure 2:
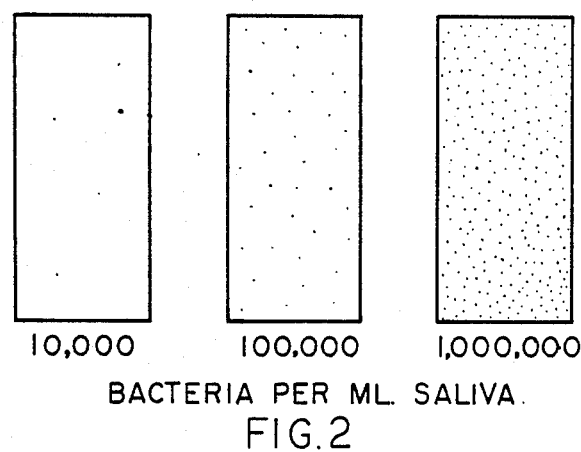
FIG. 2 is a schematic illustration of standard *Streptococcus mutan* colony density charts used with the test kit of the invention.

FIG. 2 is a schematic review of the standard colony density chart provided with the test kit which indicates in a semi-quantitative manner the *Streptococcus mutans* per milliliter of saliva as shown on the colony density chart as either 10,000; 100,000; or 1,000,000. With the use of such such a chart the incubated test sample may be compared and a semi-quantitative determination made by extrapolation of the *Streptococcus mutans* in the test sample.

A test kit designed for the semi-quantitative detection of *Streptococcus mutans* from the oral cavity contains the following items:
(a) 1 vial media on a dip-slide (media coated on both sides)
(b) 1 vial diluent solution
(c) 1 $CO_2$ generating tablet
(d) 1 strip of paraffin wax (optional)
(e) 1 bacitracin tablet (or vial or capsule containing bacitracin powder)
(f) one descriptive insert containing the directions for use
(g) one standard colony density chart (see FIG. 2.)

One liter of media is prepared according to the following formula:
90 g Mitis Salivarius Agar
150 g Sucrose
3 g Meat peptone
8 g Casein peptone
7 g Agar
0.7 g $(NH_4)_2SO_4$ Stock solutions of trypan blue dye are prepared in advance by adding 1.5 g dye to 1000 ml deionized water. Dehydrated media is loaded into an automatic sterilizer together with 100 ml stock trypan blue solution and 900 ml deionized water, to give one liter of media. Media is sterilized for 10 minutes at 121° C. and the dispensing temperature is set at 55° C. When the sterilization cycle is completed and the dispense temperature has been reached, pH is adjusted to between 7.6 and 7.7 by adding approximately 14 ml 1N NaOH. 1 ml 1% Potassium tellurite solution is added as the final component prior to dispensing of the media. The media is carefully dispensed onto both sides of plastic or glass dip-slides and are then packed into shipping cases which are refrigerated from 3° C. to 6° C., to await radiation. Cases are radiated by exposure to a Cobalt-60 source (1.45 to 1.60 Mrads). This dosage is effective in destroying any possible contaminants, and hence renders the coated media on the dip-slide or paddle sterile.

The diluent solution as prepared, for example for 1000 tests, would correspond to the following:
Sodium chloride—204 g
$K_2HPO_4$—25.68 g
$KH_2PO_4$—9.36 g The chemicals are added to a flask together with deionized water and mixed thoroughly until completely dissolved. 24 ml aliquots are dispensed into clear plastic vials, which are then capped tightly to prevent leaking or evaporation. The diluent is sterilized using a method identical to that for the media. In the test, bacitracin is added to the buffered saline diluent solution just prior to the time of use to ensure the stability of the antibiotic over a long period of time. The bacitracin USP is weighed out and combined with sorbitol (as a filler) to give about one in ten dilution. Tablets are prepared from the bacitracin/sorbitol mixture to give between 300 to 550 units, i.e. 400 to 480 units, per tablet.

The shelf life of conventional media is limited by the bacitracin which is added during preparation. Bacitracin stored at room temperature in an aqueous environment, is stable for only approximately one week or less. The storage of bacitracin in the test kit in a dry (table or powder) form, allows for long-term stability over a period of years. The shelf life of the kit is limited only by the drying out of the media and normally is stable for a period of at least several months.

When gamma irradiation is not used, one liter of conventional media contains the following:

90 g Mitis Salivarius Agar
150 g Sucrose
200 units Bacitracin
1 ml 1% Potassium tellurite
1000 ml Deionized or distilled water When gamma ray irradiation is used for sterilization, one liter of the media used contains the following:

90 g Mitis Salivarius Agar
150 g Sucrose
1 ml 1% Potassium tellurite
3 g Casein peptone
8 g Meat peptone
0.15 g Trypan blue
7 g Agar
0.7 g $(NH_4)_2SO_4$
14 ml 1N NaOH
1000 ml Deionized or distilled water The additional ingredients are added to offset effects due to radiation.

The method of use is as follows: Prepare vials of the diluent solution for use by adding a single bacitracin tablet to each vial. Cap vial and allow to stand with occasional mixing until tablet is completely dissolved. Saliva specimens are obtained by having the patient chew vigorously on a piece of paraffin supplied for approximately 3 minutes. Remove the paraffin wax from the mouth. Have patient spit into the vial containing special diluent plus bacitracin. Close the cap of the vial tightly. With the top and bottom of the vial held between forefinger and thumb respectively, shake the vial for approximately 10 seconds using an end over end motion. Loosen cap from diluent vial. Now loosen cap from the dip-slide vial and, being careful not to touch agar surfaces, remove slide from vial. Remove the cap from diluent vial, and dip the slide into the diluent by turning cap all the way down, then all the way off and remove from vial. Touch the tip of the slide to the inside edge of the vial to remove excess fluid. Place slide in original vial but do not tighten as yet. Remove carbon dioxide tablet from foil wrapper. While lifting out slide with one hand, place carbon dioxide tablet into vial with other, followed by a few drops of water. Immediately, to prevent loss of carbon dioxide, replace the dip-slide paddle into vial containing the carbon dioxide generating tablet and tighten cap. Being careful not to tip the vial, incubate the vial in upright position for 48 hours at 37° C.

After incubation the test slide is allowed to stand at room temperature for 24 hours. The agar surfaces are then examined, such as by a magnifying glass, for colony density. Typical Streptococcus mutans colonies appear as small, blue specks which are granular, and grow high off the media surface (this may be easily detected by viewing the dip-slide from the side). Especially when the test is applied to adult patients, larger, flat, glossy blue colonies may also be detected. These are most likely Streptococcus faecalis and should be disregarded in the final analysis as they bear no significance to the test. Compare the colony density with the chart provided to obtain the respective semi-quantitative bacterial count per milliliter of saliva.

What is claimed is:

1. A method for the quantitative determination of Streptococcus mutans in a test sample, which method comprises:
    (a) adding to an aseptic, aqueous, diluent solution a predetermined amount of a bacitracin composition and a test sample, taken from the oral cavity of a patient, on which a quantitative determination of Streptococcus mutans is to be made;
    (b) uniformly wetting an aseptic flat surface dip slide having at least one side coated with a selected medium and a saccharide compound with the bacitracin-test sample diluent solution, both the saccharide compound and the bacitracin present in combination on wetting the slide in a concentration insufficient to prevent the growth of Streptococcus mutans, but sufficient to prevent the growth in sufficient quantities of any interfering microorganisms;
    (c) incubating the wetted slide in an atmosphere containing carbon dioxide for a defined incubation time an temperature; and
    (d) quantitatively determining the amount of the Streptococcus mutans of the test sample by comparing the colony density of the Streptococcus mutans of the incubated slide against a visual standard comparison of Streptococcus mutans colony density thereby providing for the quantitative determination of Streptococcus mutans in the test sample.

2. The method of claim 1 wherein the test sample is saliva.

3. The method of claim 1 which includes obtaining a saliva sample from the oral cavity of the patient to be tested after the patient has masticated in the oral cavity an inert, non-toxic, chewable substance to promote the flow of saliva.

4. The method of claim 1 which includes determining the Streptococcus mutans by comparing the incubated slide against a visual standard comparison chart showing defined varying standards of Streptococcus mutans colony density in the range of from about $10^2$ to $10^7$ cfu per ml of test sample.

5. The method of claim 1 wherein the saccharide comprises sucrose.

6. The method of claim 1 wherein the diluent solution comprises a phosphate buffered saline diluent solution.

7. The method of claim 1 wherein a carbon dioxide atmosphere is generated by adding a small amount of water to a powdered composition containing a weak acid and a bicarbonate.

8. The method of claim 1 which includes irradiating the coated dip slide with gamma irradiation to render the dip slide sterile prior to use.

9. The method of claim 1 wherein the saccharide compound comprises sucrose in an amount of from about 5 to 50 percent by weight of the selected medium.

10. The method of claim 1 wherein the bacitracin composition comprises from about 300 units to 550 units per 24 milliliters of the diluent solution.

11. The method of claim 1 wherein the selected medium comprises:
    Mitis Salivarius Agar;
    Sucrose;
    postassium tellurite;
    Meat peptone;
    Casein peptone;
    Trypan blue;

Agar; and

Ammonium sulfate.

12. The method of claim 1 wherein the bacitracin composition comprises a powdered mixture of an inert filler material and bacitracin, which bacitracin composition is added to and dissolved in the aseptic diluent solution.

13. A method for the quantitative determination of *Streptococcus mutans* in a test sample, which method comprises:
   (a) dissolving in an aseptic, aqueous, diluent solution a predetermined amount of a powdered bacitracin composition and adding a saliva test sample taken from the oral cavity of a patient on which a quantitative determination of *Streptococcus mutans* is to be made;
   (b) uniformly wetting an aseptic flat surface dip slide having at least one side coated with a selected medium of agar and sucrose with the bacitracin-test sample diluent solution, both the sucrose and the bacitracin present in combination on the wetting slide in a concentration insufficient to prevent the growth of *Streptococcus mutans*, but sufficient to prevent the growth in sufficient quantities of any interfering microorganisms;
   (c) incubating the wetted slide in an incubation container having a carbon dioxide-containing atmosphere for a defined incubation time and temperature; and
   (d) quantitatively determining the amount of the *Streptococcus mutans* of the saliva test sample by comparing the colony density of the *Streptococcus mutans* of the incubated slide against a visual standard comparison of *Streptococcus mutans* colony density thereby providing for the quantitative determination of *Streptococcus mutans* in the test sample.

* * * * *